United States Patent [19]

Michel et al.

[11] 4,121,940
[45] Oct. 24, 1978

[54] ENDODONTIC FORMULA FOR TREATMENT OF ROOT CANAL

[76] Inventors: George H. Michel, 343 Oak Knoll Dr., Glendora, Calif. 91740; Donald J. Sabol, 9204 Burnet Ave., Sepulveda, Calif. 91343

[21] Appl. No.: 771,527

[22] Filed: Feb. 24, 1977

[51] Int. Cl.$^2$ ............................................. A61K 5/08
[52] U.S. Cl. ................................. 106/35; 32/15
[58] Field of Search ............................. 106/35; 32/15

[56] References Cited

U.S. PATENT DOCUMENTS 2,516,438   7/1950   Wheeler ........................... 106/35
3,205,132   9/1965   Gurney ............................. 424/49

Primary Examiner—Theodore Morris
Attorney, Agent, or Firm—Lindenberg, Freilich, Hornbaker, Wasserman, Rosen & Fernandez

[57] ABSTRACT

An endodontic formula for continuous medication of root canals is provided comprising zinc oxide, titanium oxide, paraformaldehyde, vitreous carbon, hydrocortisone, and prednisolone, all of which may be mixed with a eugenol liquid for filling the root canal. Alternatively, the hydrocortisone and prednisolone may be omitted and the amount of zinc oxide may be used to take its place.

4 Claims, No Drawings

ENDODONTIC FORMULA FOR TREATMENT OF ROOT CANAL

BACKGROUND OF THE INVENTION

This invention relates to an improved formulation for the treatment of root canals.

One of the presently preferred treatments for filling a root canal is known as the Sargenti treatment and comprises employing an "RC2B" material for obliteration of the root canal. This material consists basically of zinc oxide, a dosage amount of paraformaldehyde, along with metal salts of titanium oxide, bismuth oxide, bismuth subcarbonate, barium sulfate, and bismuth phosphate to provide adhesion and radiopacity. These are mixed with eugenol liquid for application. An additional antiseptic is also provided which comprises phenyl mercuric borate.

It has been shown that the "Sargenti treatment", as this is known, has great merit in prolonged time release type of medication of root canals. Researchers have shown that the percentage and number of other ingredients in the formulation can be changed without influencing the effectiveness of the RC2B formula, provided that the paraformaldehyde is not left out. However, while the RC2B formula is quite effective and has wide popularity, there is some contention against its use based on the fact that the formulation contains materials such as lead, bismuth and mercury, which because of their toxicity can be detrimental to health. It can be argued that the small dosages used can be tolerated, however, residual buildups must be recognized and considered.

OBJECTS AND SUMMARY OF THE INVENTION

An object of this invention is to provide an endodontic treatment for a root canal which is at least as effective as the presently used treatment but which does not contain toxic materials.

Still another object of the present invention is to provide an improved formula which is used for endodontic treatment of root canal.

The foregoing and other objects of the invention may be achieved by using a formula which replaces the toxic materials in the RC2B formula with vitreous carbon, which provides both the needed radiopacity, which is used to determine the effectiveness of the treatment, and which also provides a more controlled and prolonged release of the nascent formladehyde which insures a greater success in root canal treatment.

The novel features of the invention are set forth with particularity in the appended claims. The invention will best be understood from the following description.

DESCRIPTION OF THE PREFERRED EMBODIMENTS

Figure 1A:
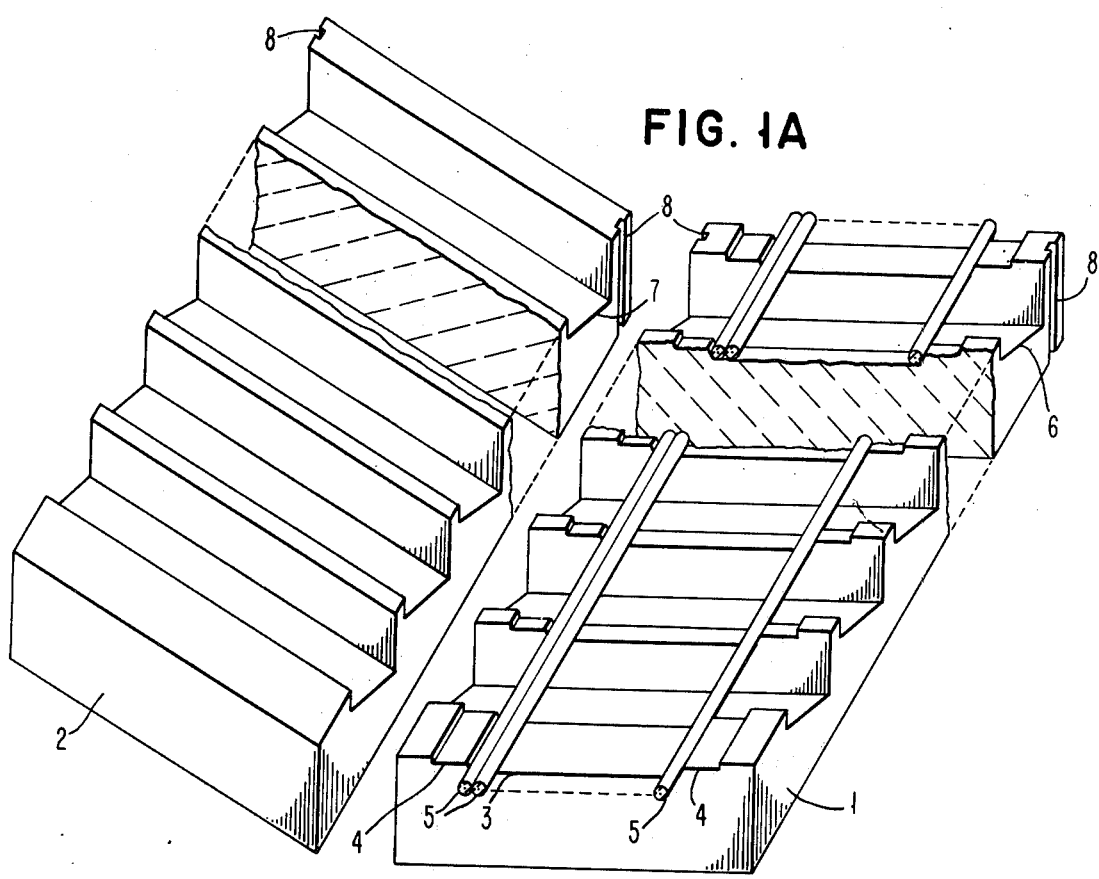
Figure 1B:
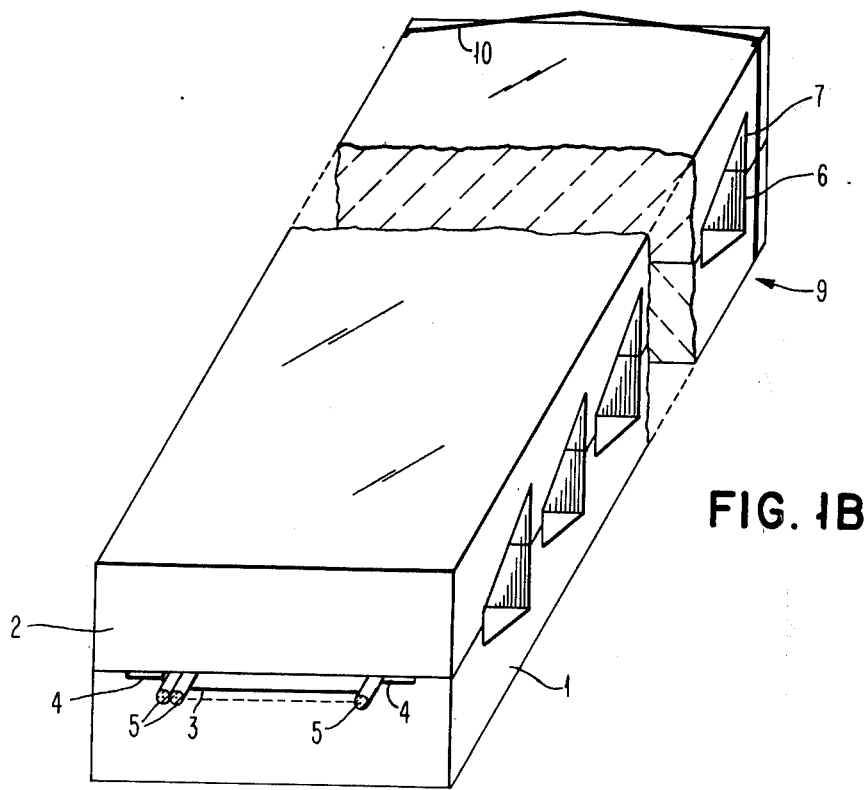
Figure 3:
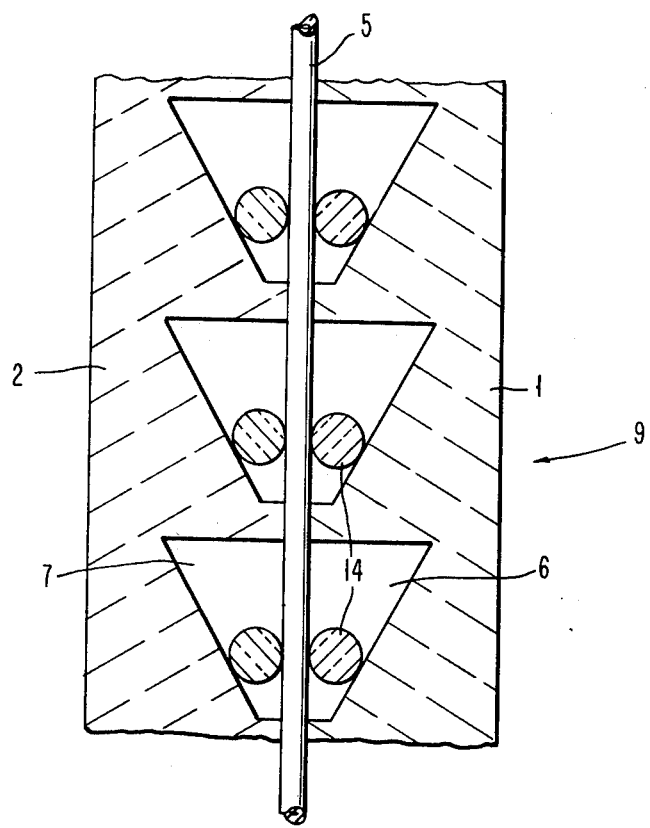
Figure 2:
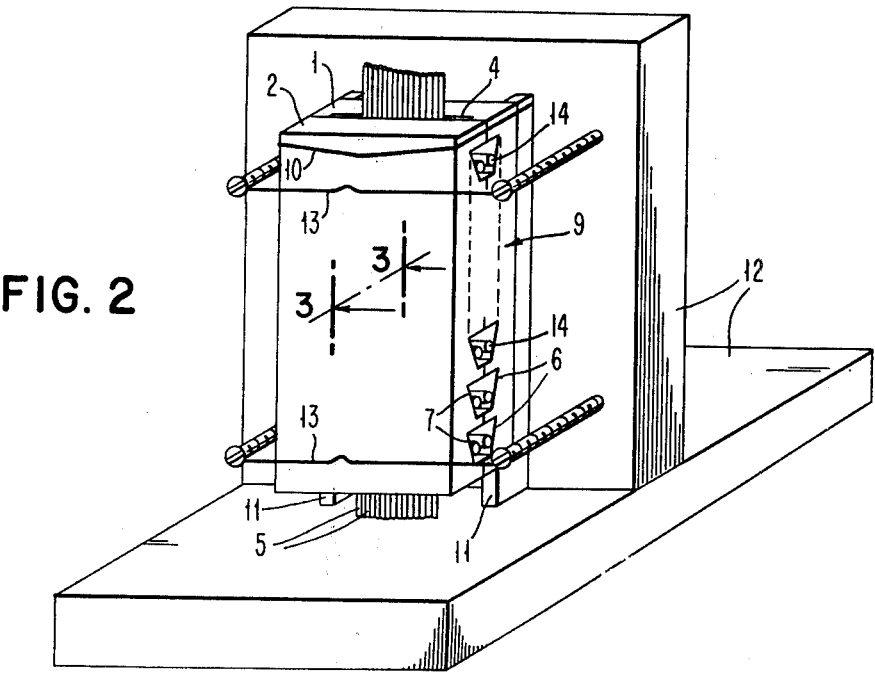
Figure 4:
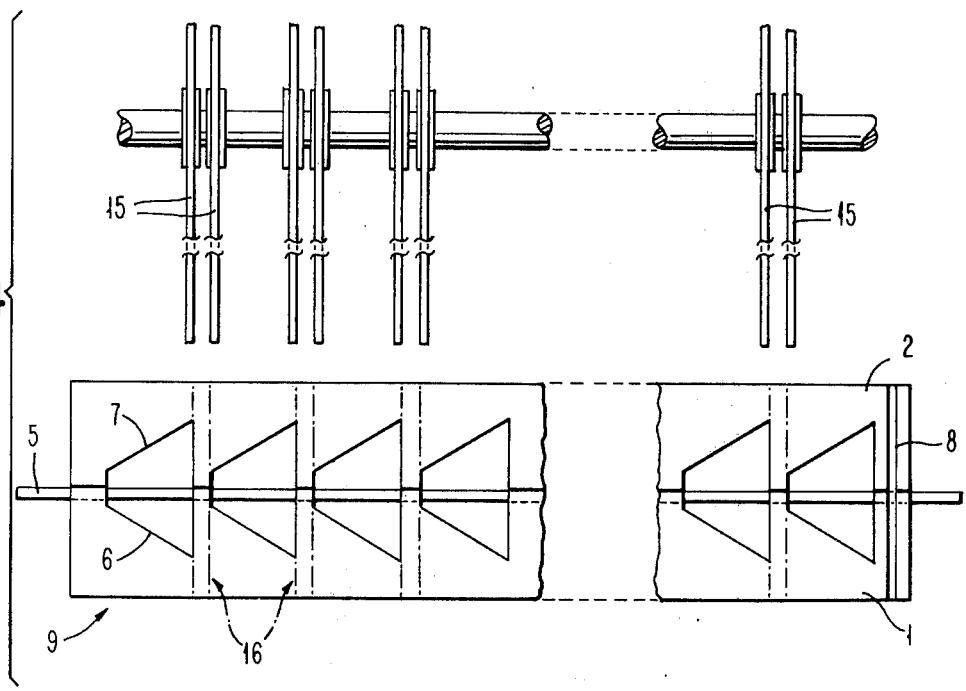
Figure 5:
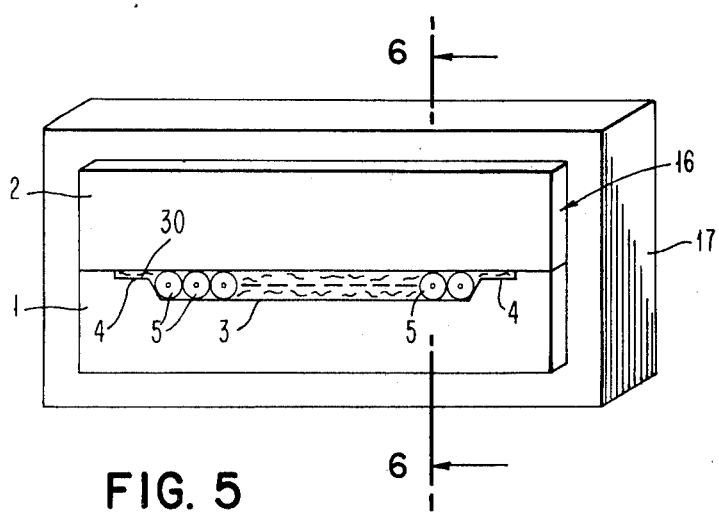
Figure 6:
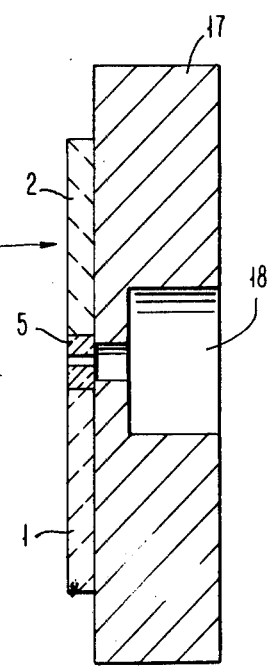
Figure 7:
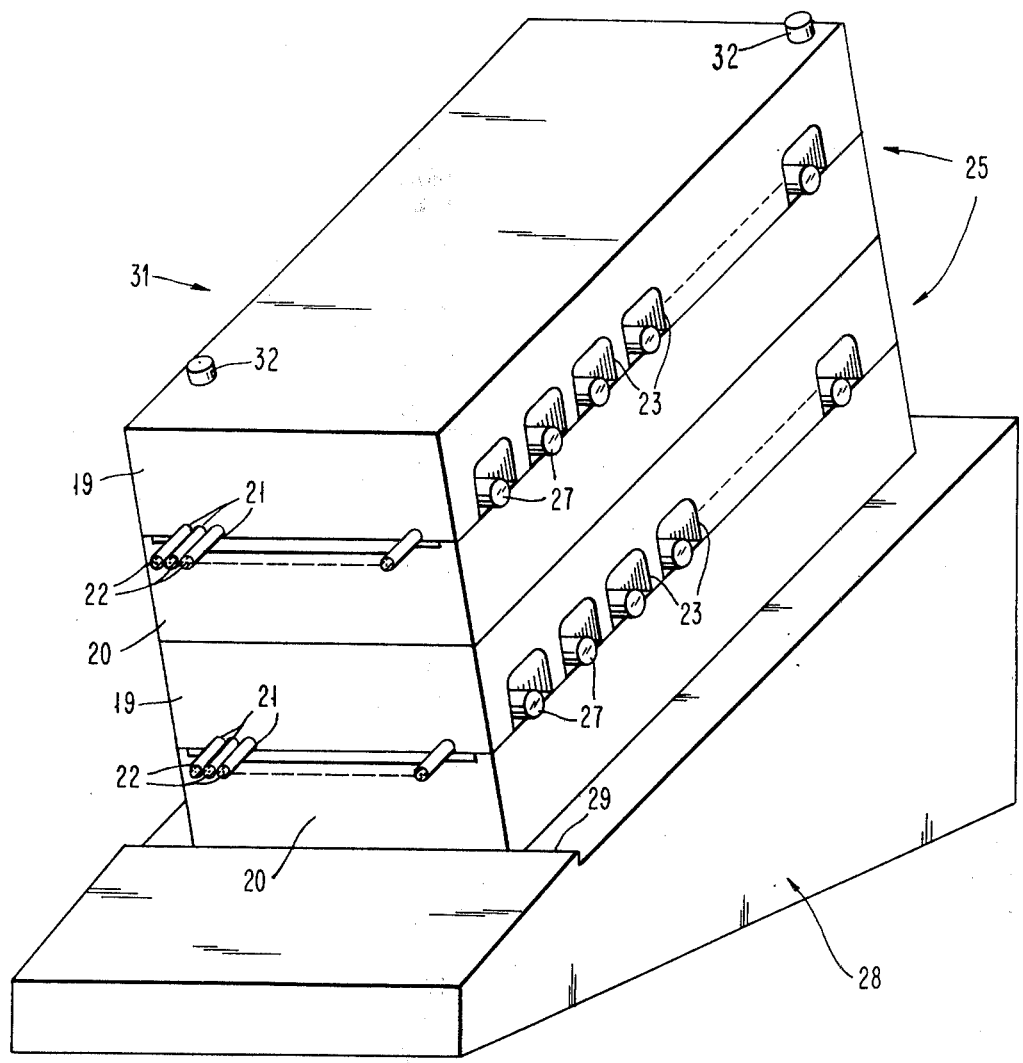
Figure 8:
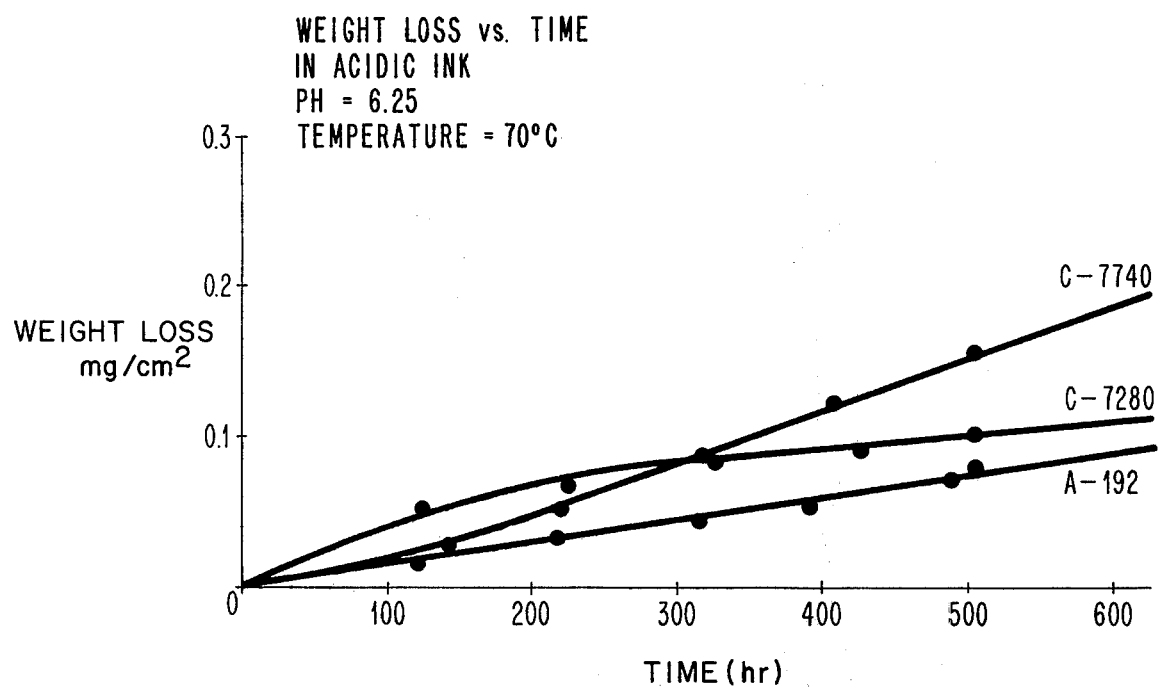
Figure 9:
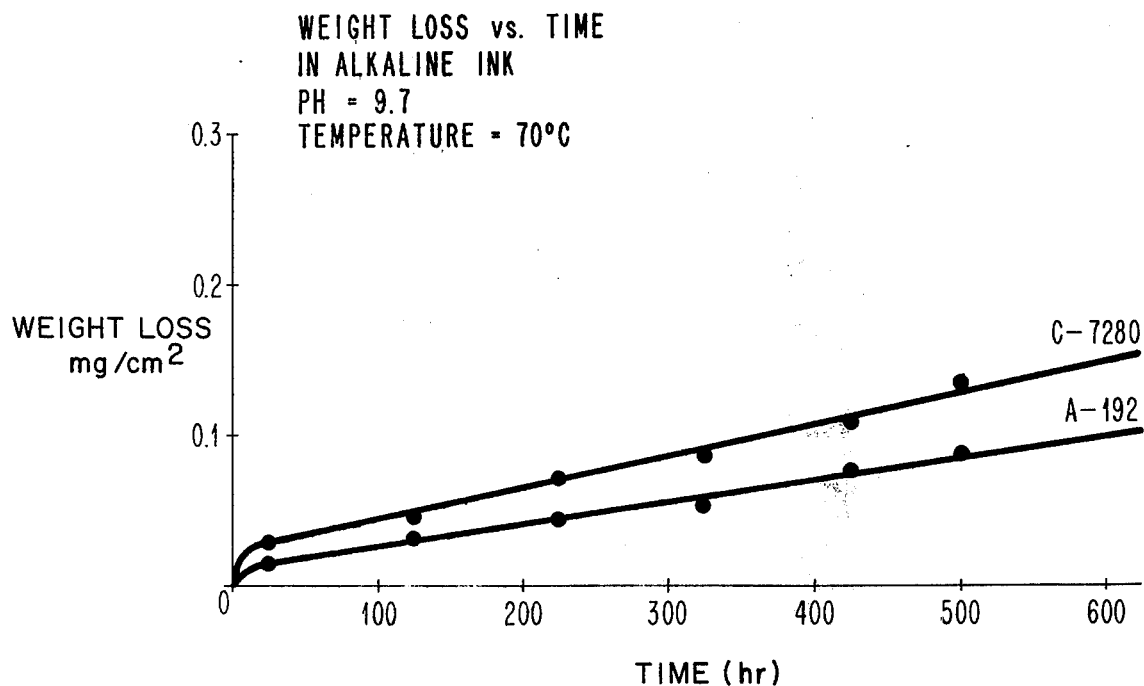

A preferred formulation, in accordance with this invention, contains by weight, 6.5% paraformaldehyde, 5% vitreous carbon, titanium dioxide 4.00%, zinc oxide 83.09%, hydrocortisone 1.2%, and prednisolone 0.21%. If desired, the prednisolone and hydrocortisone may be omitted and the amount of zinc oxide in the formulation may then be increased by 1.41% to take their place. It has been found that varying precentages of the materials used in the formula can be used and so, in accordance with this invention, the formula, by weight, may include vitreous carbon 0.2 to 30%, titanium dioxide 0.05% to 30%, zinc oxide 0.05% to 84.00%, hydrocortisone 05 to 8.00%, prednisolone 0% to 8% and paraformaldehyde 5% to 25%. The prednisolone is a well known material, made and sold by Pfizer Company.

The kind of vitreous carbon to be used is the same as is used, for example, in dental implants, and is described, for example, in U.S. Pat. No. 2,457,224. It may be obtained from Fluorocarbon Corporation located at 875 Rose Place, Anaheim, California.

In order to determine the effectiveness of the new and improved formula, in accorcance with this invention, it has been compared with the RC2B formula for a control, with both formulas being subjected to bacteriostatic tests.

METHOD OF ANALYSIS

Basically a standard pour plate in which a given number of pure bacteria cultures, plus the test mixture in a known amount was mixed with a nutrient medium. After a predetermined period of time to provide for optimal growth for the organism selected, an observation was made for inhibition or positive growth.

Three organisms were selected, based on their history of having been associated with dental diseases. The three were as follows:

1. Staphylococcus aureus (S. aureus)
2. Lactobacillus salivarius (L. salivarius)
3. Lactobacillus acidolphilus (L. acidolphilus)

Orange serum agar was used for the Lactobacillus species and standard plate count agar was used for the Staphylococcus species. All plates after pouring were then incubated at 37° C. for a period of 72 hours.

The exact makeup of each plate was as follows:
1. A known quantity of the test material was weighed into the plate.
2. A known number of test organisms were then pipetted into the plate. An overlaying of the growth medium was poured in, followed by rapid agitation, in which an even mixture of organisms, test material, and media were achieved, incubated and then evaluated.

The level of organisms per plate was as follows:
1. S. aureus — 27,000,000.
2. L. acidolphilus — 600,000.
3. L. salivarius — 4,000,000.

| Test Results | | | | |
|---|---|---|---|---|
| | | Microorganisms used in test | | |
| Sample | Quantity tested, mg. | S. Aureus | L Salivarius | L Acidolphilus |
| 1. R-0136- (RC2B) | 250 | — | — | — |
| | 100 | — | — | — |
| | 50 | — | — | — |
| | 10 | ± | + | + |
| 2. R-0136-E (Our formula) | 250 | — | — | — |
| | 100 | — | — | — |
| | 50 | — | — | — |
| | 10 | + | + | + |

(—) No growth means - apparent complete inhibition
(±) Inconclusive means partial inhibition
(+) Growth means - no apparent inhibition.

From the foregoing, it will be seen that, as far as inhibiting bacillus growth, a formulation in accordance with this invention is as effective as the Sargenti RC2B formula. However, the present invention does not contain the potentially toxic metals, such as lead, bismuth and mercury. Further, it has been found that a formulation in accordance with this invention by correlation with a control provides a more controlled and prolonged release of the nascent formaldehyde which insures greater success in root canal treatment. The decrease in release time is on the order of at least two times that of the RC2B formula.

Makeup of the formula, in accordance with this invention is quite simple. The various components, in powder form are thoroughly mixed with one another. The application of the formula to a root canal, by way of example of proportions which are preferred but which should not be considered as a limitation upon the invention, are, 300 milligrams of the formula powder are mixed with six drops of the eugenol liquid. Eugenol liquid is a well known liquid formulation used by dentists. It is purchased from a number of suppliers, one of these being Merk Company.

The powder and eugenol liquid are mixed to have the consistency of paste. For application, the spiral drill which is used for making the root canal opening is usually dipped into the paste and then is inserted into the root canal opening. This is done repeatedly until the opening is filled, at which time the opening is capped in the usual fashion. Another approach is to add terra-cortril (TCM) manufactured by Pfizer. Usually, one drop of terra-cortril powder, plus eugenol paste. This is mixed with and processed in the same manner as described above. The material, in accordance with this invention, may be provided in tablet form to provide exact dosage and permit easier handling by the dentists.

From the foregoing, it may be seen that a novel and improved formula for achieving endodontic treatment of a root canal is provided wherein potentially harmful metals are eliminated and replaced by a substance which has been shown to be harmless to the body, and yet which provides both required radiopacity and most importantly prolongs the application of the medication and sterilization required for insuring the success of the root canal treatment.

In the claims:

1. A formula for endodontic treatment of a root canal comprising a mixture by weight of:
   0.5% to 30% of titanium oxide, 0.05% to 84.00% of zinc oxide, 0% to 8% of hydrocortisone, 0% to 8% of prednisolone, 5% to 25% of paraformaldehyde, and 0.2% to 30% of vitreous carbon.

2. A formula for endodontic treatment of a root canal comprising a mixture by weight of:
   paraformaldehyde, 6.5%; vitreous carbon, 5%; titanium oxide, 4%; zinc oxide, 83.09%; hydrocortisone, 1.2%; and prednisolone, 0.21%.

3. A formula for endodonctic treatment of a root canal comprising a mixture by weight of:
   paraformaldehyde, 6.5%; vitreous carbon, 5%; titanium oxide, 4%; and zinc oxide 84.5%.

4. In a formula for a treatment of a root canal which consists basically of zinc oxide, paraformaldehyde, and metal salts of tatanium oxide, bismuth oxide, bismuth subcarbonate, barium sulphate, lead oxide, bismuth phosphate and phenyl mercuric borate, the improvement comprising:
   replacing the bismuth oxide, bismuth subcarbonate, barium sulphate, lead oxide, bismuth phosphate and phenyl mercuric borate with vitreous carbon.

* * * * *